US008524279B2

(12) United States Patent
Snyder et al.

(10) Patent No.: US 8,524,279 B2
(45) Date of Patent: Sep. 3, 2013

(54) SPRAY DRYING METHODS AND RELATED COMPOSITIONS

(75) Inventors: Herman E. Snyder, Pacifica, CA (US); Michael J. Vosberg, San Carlos, CA (US); Christopher M. Varga, Redwood City, CA (US)

(73) Assignee: Novartis AG, Basel (CH)

( * ) Notice: Subject to any disclaimer, the term of this patent is extended or adjusted under 35 U.S.C. 154(b) by 730 days.

(21) Appl. No.: 10/284,960

(22) Filed: Oct. 31, 2002

(65) Prior Publication Data

US 2003/0124193 A1  Jul. 3, 2003

Related U.S. Application Data

(60) Provisional application No. 60/336,538, filed on Nov. 1, 2001.

(51) Int. Cl.
*A61K 9/14* (2006.01)

(52) U.S. Cl.
USPC .......................................... 424/489; 424/499

(58) Field of Classification Search
USPC ........................................................ 424/489
See application file for complete search history.

(56) References Cited

U.S. PATENT DOCUMENTS

| | | | |
|---|---|---|---|
| 3,770,207 A | 11/1973 | Muller et al. | |
| 3,790,079 A | 2/1974 | Berglund et al. | |
| 3,825,188 A | 7/1974 | Doering | |
| 4,035,317 A | 7/1977 | Gershberg | |
| 4,052,255 A | 10/1977 | Hackbarth et al. | |
| 4,127,235 A | 11/1978 | Klaile et al. | |
| 4,221,339 A | 9/1980 | Yoshikawa | |
| 4,261,793 A | 4/1981 | Nakamura et al. | |
| 4,305,210 A | 12/1981 | Christensen et al. | |
| 4,476,804 A | 10/1984 | Glatt et al. | |
| 4,486,435 A | 12/1984 | Schmidt et al. | |
| 4,540,602 A | 9/1985 | Motoyama et al. | |
| 4,590,206 A | 5/1986 | Forrester et al. | |
| 4,702,799 A | 10/1987 | Tuot | |
| 4,721,709 A | 1/1988 | Seth et al. | |
| 4,748,034 A | 5/1988 | de Rham | |
| 4,760,093 A | 7/1988 | Blank et al. | |
| 4,784,878 A | 11/1988 | Haak | |
| 4,794,167 A | 12/1988 | Lindner et al. | |
| 4,818,424 A | 4/1989 | Evans et al. | |
| 4,835,187 A | 5/1989 | Reuter et al. | |
| 4,866,051 A | 9/1989 | Hunt et al. | |
| 4,871,489 A | 10/1989 | Ketcham | |
| 4,952,402 A | 8/1990 | Sparks et al. | |
| 5,000,888 A | 3/1991 | Kilbride, Jr. et al. | |
| 5,009,367 A | 4/1991 | Nielsen | |
| 5,017,372 A | 5/1991 | Hastings | |
| 5,026,550 A | 6/1991 | Aeschbach et al. | |
| 5,038,769 A | 8/1991 | Krauser | |
| 5,066,522 A | 11/1991 | Cole et al. | |
| 5,221,731 A | 6/1993 | Weymans et al. | |
| 5,232,707 A | 8/1993 | Lokensgard | |
| 5,260,306 A | 11/1993 | Boardman et al. | |
| 5,269,980 A | 12/1993 | Levendis et al. | |
| 5,279,708 A | 1/1994 | Wood et al. | |
| 5,384,133 A | 1/1995 | Boyes et al. | |
| 5,482,927 A | 1/1996 | Maniar et al. | |
| 5,518,709 A | 5/1996 | Sutton et al. | |
| 5,580,856 A | 12/1996 | Prestrelski et al. | |
| 5,607,697 A | 3/1997 | Alkire et al. | |
| 5,622,657 A | 4/1997 | Takada et al. | |
| 5,624,530 A | 4/1997 | Sadykhov et al. | |
| 5,628,937 A | 5/1997 | Oliver et al. | |
| 5,648,096 A | 7/1997 | Gander et al. | |
| 5,651,990 A | 7/1997 | Takada | |
| 5,667,806 A | 9/1997 | Kantor | |
| 5,687,905 A | 11/1997 | Tsai | |
| 5,723,269 A * | 3/1998 | Akagi et al. | .................. 424/497 |
| 5,741,478 A | 4/1998 | Osborne et al. | |
| 5,776,491 A | 7/1998 | Allen, Jr. et al. | |
| 5,800,598 A | 9/1998 | Chein et al. | |
| 5,807,576 A | 9/1998 | Allen, Jr. et al. | |
| 5,855,913 A | 1/1999 | Hanes et al. | |
| 5,874,029 A * | 2/1999 | Subramaniam et al. | ........ 264/12 |
| 5,874,064 A | 2/1999 | Edwards et al. | |
| 5,922,253 A | 7/1999 | Herbert et al. | |

(Continued)

FOREIGN PATENT DOCUMENTS

| | | |
|---|---|---|
| EP | 0072046 | 2/1983 |
| EP | 0260971 | 3/1988 |

(Continued)

OTHER PUBLICATIONS

Brandenberger et al (A new multinozzle encapsulation/immobilization system to produce uniform beads of alginate. Journal of Biotechnology, vol. 63, 1998, pp. 73-80).*

Wikipedia (http://en.wikipedia.org/wiki/Bactericidal/permeability-increasing_protein; (downloaded on Nov. 19, 2012)).*

Prube et al (Production of Spherical Beads by JetCutting. Chemical Engineering & Technology. vol. 23 Issue 12, pp. 1105-1110 (2000)).*

Austen J. Woolfe et al. "Spray Dried Powders for Pulmonary or Nasal Administration," United States Patent Application Publication No. US 2002/0081266 A1, Pub. Date: Jun. 27, 2002.

Kevin M.G. Taylor and Stephen J. Farr, "Liposomes for Drug Delivery to the Respiratory Tract." Drug Development and Industrial Pharmacy 1993, 19(1&2), p. 124-142.

Roland Bodmeier and Huagang Chen, "Preparation of Biodegradable Poly(+)lactide Microparticles Using a Spray-Drying Technique." J. Pharm. Pharmocol. 1988 , 40:, p. 754-757.

(Continued)

*Primary Examiner* — Jake M. Vu
(74) *Attorney, Agent, or Firm* — Janah & Associates, PC

(57) ABSTRACT

A method and apparatus are provided for atomizing a liquid under dispersal conditions suitable for spray drying at a commercial plant scale. In one embodiment, a liquid atomizer has a structural body adapted for connection with a spray dryer and a plurality of atomizing nozzles. Each of the atomizing nozzles includes a liquid nozzle adapted to disperse a supply of liquid and a gas nozzle adapted to disperse a supply of gas. In another embodiment, a process for producing a powder blend of at least two target substances in a single processing step is provided.

26 Claims, 10 Drawing Sheets

(56) References Cited

U.S. PATENT DOCUMENTS

| | | | |
|---|---|---|---|
| 5,924,216 A | 7/1999 | Takahashi | |
| 5,964,416 A | 10/1999 | Jaeger et al. | |
| 5,970,974 A | 10/1999 | Van Der Linden et al. | |
| 5,976,574 A | 11/1999 | Gordon | |
| 5,985,248 A | 11/1999 | Gordon et al. | |
| 5,985,309 A | 11/1999 | Edwards et al. | |
| 5,993,805 A | 11/1999 | Sutton et al. | |
| 5,997,848 A | 12/1999 | Patton et al. | |
| 6,001,336 A | 12/1999 | Gordon | |
| 6,015,546 A | 1/2000 | Sutton et al. | |
| 6,017,310 A | 1/2000 | Johnson et al. | |
| 6,022,525 A | 2/2000 | Sutton et al. | |
| 6,051,256 A * | 4/2000 | Platz et al. | 424/489 |
| 6,051,257 A * | 4/2000 | Kodas et al. | 424/489 |
| 6,077,543 A * | 6/2000 | Gordon et al. | 424/489 |
| 6,117,455 A | 9/2000 | Takada et al. | |
| 6,123,924 A | 9/2000 | Mistry et al. | |
| 6,149,941 A | 11/2000 | Schwarz et al. | |
| 6,153,129 A | 11/2000 | Herbert et al. | |
| 6,165,511 A | 12/2000 | Schwarz et al. | |
| 6,308,434 B1 | 10/2001 | Chickering, III et al. | |
| 6,331,290 B1 | 12/2001 | Morgan | |
| 6,331,310 B1 | 12/2001 | Roser et al. | |
| 6,365,190 B1 | 4/2002 | Gordon et al. | |
| 6,383,810 B2 | 5/2002 | Fike et al. | |
| 6,416,739 B1 | 7/2002 | Rogerson et al. | |
| 6,423,344 B1 | 7/2002 | Platz et al. | |
| 6,455,028 B1 | 9/2002 | Wulffhart et al. | |
| 6,503,480 B1 | 1/2003 | Edwards et al. | |
| 6,565,885 B1 | 5/2003 | Tarara et al. | |
| 6,572,893 B2 | 6/2003 | Gordon et al. | |
| 6,582,728 B1 | 6/2003 | Platz et al. | |
| 6,592,904 B2 | 7/2003 | Platz et al. | |
| 6,656,492 B2 | 12/2003 | Kajiyama et al. | |
| 2002/0081266 A1 | 6/2002 | Woolfe et al. | |
| 2002/0175225 A1 | 11/2002 | Boersen et al. | |
| 2003/0124193 A1 | 7/2003 | Snyder et al. | |
| 2003/0203036 A1 | 10/2003 | Gordon et al. | |
| 2003/0215514 A1 | 11/2003 | Platz et al. | |

FOREIGN PATENT DOCUMENTS

| | | |
|---|---|---|
| EP | 0344375 | 12/1989 |
| EP | 0408801 | 1/1991 |
| EP | 0461930 | 12/1991 |
| EP | 469725 | 2/1992 |
| EP | 512693 | 11/1992 |
| EP | 0344375 | 12/1993 |
| EP | 0580428 | 1/1994 |
| EP | 0611567 | 8/1994 |
| EP | 628331 | 12/1994 |
| EP | 674541 | 10/1995 |
| EP | 0408801 | 11/1995 |
| EP | 681843 | 11/1995 |
| EP | 709085 | 5/1996 |
| EP | 972526 | 1/2000 |
| EP | 1004349 | 5/2000 |
| GB | UK 473471 | 10/1937 |
| GB | UK 621785 | 4/1949 |
| GB | 2105189 | 3/1983 |
| WO | WO 88/07870 | 10/1988 |
| WO | WO 90/11139 | 10/1990 |
| WO | WO 91/16882 | 11/1991 |
| WO | WO 92/18164 | 10/1992 |
| WO | WO 93/07465 | 4/1993 |
| WO | WO 94/08627 | 4/1994 |
| WO | WO 95/00127 | 1/1995 |
| WO | WO 95/13864 | 5/1995 |
| WO | WO 95/23613 | 9/1995 |
| WO | WO 95/24183 | 9/1995 |
| WO | WO 95/31479 | 11/1995 |
| WO | WO 96/03978 | 2/1996 |
| WO | WO 96/05809 | 2/1996 |
| WO | WO 96/09814 | 4/1996 |
| WO | WO 96/11580 | 4/1996 |
| WO | WO 96/15814 | 5/1996 |
| WO | WO 96/32096 | 10/1996 |
| WO | WO 96/32149 | 10/1996 |
| WO | WO 96/40076 | 12/1996 |
| WO | WO 97/28788 | 8/1997 |
| WO | WO 97/36574 | 10/1997 |
| WO | WO 97/41833 | 11/1997 |
| WO | WO 97/44067 | 11/1997 |
| WO | WO 9741833 | 11/1997 |
| WO | WO 98/01228 | 1/1998 |
| WO | WO 98/29096 | 7/1998 |
| WO | WO 98/29098 | 7/1998 |
| WO | WO 98/31346 | 7/1998 |
| WO | WO 9829096 | 7/1998 |
| WO | WO 98/47493 | 10/1998 |
| WO | WO 99/16419 | 4/1999 |
| WO | WO 99/16422 | 4/1999 |
| WO | WO 99/17742 | 4/1999 |
| WO | WO 99/30834 | 6/1999 |
| WO | WO 99/31019 | 6/1999 |
| WO | WO 99/32083 | 7/1999 |
| WO | WO 9964014 | 12/1999 |
| WO | WO 9964014 A1 * | 12/1999 |
| WO | WO 00/00176 | 1/2000 |
| WO | WO 00/09084 | 2/2000 |
| WO | WO 00/10541 | 3/2000 |
| WO | WO 00/12278 | 3/2000 |
| WO | WO 00/13668 | 3/2000 |
| WO | WO 00/66256 | 11/2000 |
| WO | WO 00/76673 | 12/2000 |
| WO | WO 01/03673 | 1/2001 |
| WO | WO 01/13885 | 3/2001 |
| WO | WO 01/15664 | 3/2001 |
| WO | WO 01/45731 | 6/2001 |
| WO | WO 01/64188 | 9/2001 |
| WO | WO 01/87278 | 11/2001 |
| WO | WO 02/09869 | 2/2002 |
| WO | WO 02/15880 | 2/2002 |
| WO | WO 02/078675 | 10/2002 |
| WO | WO 03/000202 | 1/2003 |

OTHER PUBLICATIONS

Barj et al. "Submicronic MgAl2O4 Powder Synthesis in Supercritical Ethanol." J. of Materials Sci. vol. 27. No. 8 p. 2187-2192 (1992).

Prusse, et al., "Production of Spherical Beads by Jet Cutting," 23 ed., vol. 12, Chem. Eng. Technol. (2000).

Office Action in Duropean Application. No. 08 16 0325, (Oct. 2008).

EPO Communication dated May 15, 2007 for European Application No. 02776395.2.

H. Brandenberger article, "A New Multinozzle Encapsulation/Immobilisation System to Produce Uniform Beads of Alginate.", (1998).

* cited by examiner

SPRAY DRYING METHODS AND RELATED COMPOSITIONS

RELATED APPLICATIONS

The present application claims the benefit of U.S. Provisional Application No. 60/336,538 filed on Nov. 1, 2001.

FIELD OF THE INVENTION

The present invention relates generally to liquid atomization. More particularly, the present invention relates to a method and apparatus for providing atomized liquids for use in a commercial spray-drying environment. The invention further relates to methods of spray drying to form particulates and the particulates formed thereby, including the single step production of uniform powder blends. The invention is particularly suited for producing particles for pulmonary administration.

BACKGROUND OF THE INVENTION

In recent years, certain drugs have been sold in compositions suitable for forming a drug dispersion for oral inhalation (pulmonary delivery) to treat various conditions in humans. Such pulmonary drug delivery compositions are designed to be delivered by inhalation by the patient of a drug dispersion so that the active drug within the dispersion can reach the lung. It has been found that certain drugs delivered to the lung are readily absorbed through the alveolar region directly into blood circulation. Pulmonary delivery is particularly promising for the delivery of active agents (proteins, polypeptides, high-molecular-weight polysaccharides, and nucleic acids) which are difficult to deliver by other routes of administration. Such pulmonary delivery can be effective both for systemic delivery and for localized delivery to treat diseases of the lungs.

Pulmonary drug delivery can itself be achieved by different approaches, including liquid nebulizers, propellant-based metered dose inhalers (MDI's), and dry powder inhaler (DPI) devices. DPIs are particularly promising for delivering drugs that may be readily formulated as dry powders. Many otherwise labile active agents may be stably stored as lyophilized or spray-dried powders by themselves or in combination with suitable powder carriers.

The ability to deliver pharmaceutical compositions as dry powders, however, is problematic in certain respects. The dosage of many pharmaceutical compositions is often critical, so it is desirable that dry powder delivery systems be able to accurately, precisely, and reliably deliver the intended amount of drug. Moreover, many pharmaceutical compositions are quite expensive. Thus, the ability to efficiently formulate, process, package, and deliver the dry powders with a minimal loss of drug is critical.

A particularly promising approach for the pulmonary delivery of dry powder drugs utilizes a hand-held device with a hand pump for providing a source of pressurized gas. The pressurized gas is abruptly released through a powder dispersion device, such as a venturi nozzle, and the dispersed powder made available for patient inhalation. While advantageous in many respects, such hand-held devices are problematic in a number of other respects. The particles being delivered are often less than 5 µm in size, making powder handling and dispersion more difficult than with larger particles. The problems are exacerbated by the relatively small volumes of pressurized gas available using hand-actuated pumps. In particular, venturi dispersion devices are unsuitable for difficult-to-disperse powders when only small volumes of pressurized gas are available with the handpump. Another requirement for hand-held and other powder delivery devices is efficiency. High device efficiency in delivering the drug to the patient with the optimal size distribution for pulmonary delivery is desirable for a commercially viable product. Conventional techniques used to deliver medication do not have the delivery efficiency required for commercialization. The ability to achieve both adequate dispersion and small dispersed volumes is a significant technical challenge that requires that each unit dosage of the powdered composition be readily and reliably dispersible.

Spray drying is a conventional chemical processing unit operation used to produce dry particulate solids from a variety of liquid and slurry starting materials. The use of spray drying for the formulation of dry powder pharmaceuticals, including proteins and peptides for pulmonary administration, is known. Spray drying processes for producing fine powders for inhalation are disclosed in U.S. Pat. Nos. 5,976,574, 5,985,248, 6,001,336, 6,051,256, 6,077,543, and 6,423,344 and PCT Publications WO 96/32149, WO 99/16419, WO 01/00312, WO 01/85136 and in WO 02/09669 which are hereby incorporated in their entirety by reference. Additional spray drying processes are disclosed in WO 97/13503 and U.S. Pat. Nos. 5,622,657, 5,723,269, 6,149,941 and 6,165,511, hereby incorporated in their entirety by reference.

The use of spray drying for the preparation of active agent compositions, including proteins, polypeptides, high molecular weight polysaccharides, and nucleic acids, can be problematic since such active agents are often labile and subject to degradation when exposed to high temperatures and other aspects of the spray drying process. Excessive degradation of the active agents can lead to drug formulations lacking in the requisite purity. It can also be difficult to control particle size and particle size distribution in compositions produced by spray drying. For pulmonary delivery, the average particle size should be maintained below 10 µm, preferably below 5 µm, such as in the range from 0.4 µm to 5 µm, and the amount of the composition comprising particles outside of the target size range should be minimized. Preferably, at least 90% by weight of the powder will have a particle size in the range from 0.1 µm to 7 µm. More preferably, at least 95% will have a size in the range from 0.4 µm to 5 µm. Moreover, it can sometimes be difficult to achieve a desired low moisture content sufficient for physical and chemical stability in the final particulate product, particularly in an economic manner. Also, it has been difficult to produce the small particles necessary for pulmonary delivery in an efficient manner. For high value macromolecular drugs, collection efficiencies (i.e., the amount of particulate drug recovered from the process in a useable form) should be above 80% by weight, preferably above 90% by weight, and desirably above 95% by weight.

Due to the difficulties in particle collection and efficient aerosol dispersion, the use of larger carrier particles (i.e. up to an order of magnitude) such as lactose in combination with the active agent particles is well known in the pulmonary drug delivery field. The combination of these carrier particles with the active agent particles results in a final product consisting of a powder blend of these two constituents. These powder blends are typically prepared by separately producing each of the blend constituents, and then combining the two constituents in yet another processing step, typically mechanically mixing the two dry particle constituents in a mixer such as a Turbula mixer under optimized conditions. However, there exists a need to effectively blend significant quantities of respirable particle sized powders.

While spray drying has been used to prepare fine powders of active agents in laboratory scale equipment, commercial spray dryers are not designed to produce such fine powders in the pulmonary size range. In scaling up a spray-drying process from the laboratory or even pilot plant scale to the commercial scale, certain inefficiencies may become manifest. For example, the solvent content of the product may increase if the drying efficiency is not adequately scaled. As part of the scale-up to commercial processing, which may include as much as a tenfold or greater increase in throughput from a pilot-plant scale, careful consideration must be given in order to preserve product properties.

Various atomizers have been used in the spray drying of pharmaceutical powders. Droplet size and droplet size distribution are determined by the selection of the atomizer and operating conditions. These include gas assisted two-fluid nozzles, rotary atomizers and ultrasonic atomizers comprising an oscillating horn to create surface instabilities resulting in droplet formation. Examples of each of these various atomizers are disclosed in the patents cited above.

Sonic air-assisted two-fluid atomization nozzles (two-fluid nozzles) involve impacting liquid bulk with high velocity gas, utilizing the kinetic energy of a sonic or supersonic velocity gas stream to create the liquid surface area. Sprays of low viscosity feed are characterized by low mean droplet sizes. Formation of sprays having a mass median diameter of 15-20 microns are well established for such two-fluid nozzles. With more viscous feeds, larger mean droplet sizes are produced with a wider particle size distribution. Among the variables affecting mean droplet size for two-fluid nozzles, the air to liquid mass ratio ($M_{air}:M_{liq}$) and design details of the given atomizer are perhaps the most important variables.

In rotary atomization, the feed liquid is centrifugally accelerated to high velocity before being discharged into an air-gas atmosphere. The liquid is distributed centrally on a rotating wheel/disc/cup and extends over the rotating surface as a thin film. Operating variables that influence droplet size produced from atomizer wheels are speed of rotation, wheel diameter, wheel design (number and geometry of vanes or bushings), feed rate, viscosity of feed and air, density of feed and air, and surface tension of feed. Two-fluid nozzles are capable of producing smaller droplets compared to rotary atomizers. It is perhaps for their ability to produce smaller droplets that two-fluid nozzles are currently more commonly used in spray drying applications for producing particles for pulmonary administration.

More recently, interest has focused on electrically assisted ultrasonic atomizers. Such interest has in part been prompted by the need to develop a technique to atomize products that are non Newtonian, highly viscous, and have long chain molecular structures, and that form only strings or filaments from rotary atomizers and liquids that require very high pressure for effective atomization from pressure nozzles.

Whichever atomizer is selected, its design must be scaled when moving from laboratory or pilot scale capacity to larger, commercial scales. Careful consideration must be given to ensure satisfactory maintenance of the initial droplet formation. Failure to provide suitable initial droplet conditions could lead to significant differences in product characteristics of the final spray-dried particulates.

The above describes some of the problems currently encountered in the development of spray drying processes for pharmaceutical application, particularly with respect to spray drying powders for pulmonary administration. Moreover, it can be difficult to achieve a desired low moisture content required for physical and chemical stability in the final particulate product, particularly in an economic manner. Finally and perhaps most importantly, it has been difficult to produce the small particles necessary for pulmonary delivery in an efficient manner on a large scale suitable for commercial applications.

It is therefore desirable to provide improved methods and apparatuses for the spray drying of pharmaceuticals for use in pulmonary and other drug delivery applications. In particular, it is desirable to provide improved methods and apparatuses suitable for such applications at the commercial plant scale which maintain product properties observed at smaller pilot scales.

It is further desirable to produce a uniform powder blend for pharmaceutical applications, particularly for particles sized for respiratory administration, which can be produced in a single step. Such a simplified process eliminates the need for intermediate storage, reduces the risk of product contamination and/or product loss, and reduces capital equipment costs thereby reducing the time and costs of the current multi-step blending processes. Furthermore, such single step production of powder blends eliminates the optimization of current mechanical blending techniques, which is an extremely time consuming process.

BRIEF SUMMARY OF THE INVENTION

Accordingly, embodiments of the invention provide a method and apparatus for atomizing a liquid under dispersal conditions suitable for spray drying at a commercial plant scale. In one embodiment, a gas assisted liquid atomizer comprises a structural body adapted for connection with a spray dryer and a plurality of atomizing nozzles. Each of the atomizing nozzles includes a liquid nozzle adapted to disperse a liquid and a gas nozzle adapted to disperse a gas. In one embodiment the gas nozzle is coaxial with the liquid nozzle and positioned around the liquid nozzle.

Each of the atomizing nozzles may be tilted from a centerline of the structural body by an angle between 0°-180°, preferably 10° and 40° to minimize spray plume interaction. In one embodiment the tilt angle from the centerline is between 15° and 25°.

According to another embodiment, the atomizer may also comprise a supplemental gas nozzle, which may have an axis substantially along the centerline of the structural body. The supplemental nozzle may further assist in minimizing spray plume interactions, as well as enabling control over a variety of final powder characteristics. For example, the supplemental nozzle may be adapted to disperse a gas and/or a liquid to modify the chemical composition of the atomized droplets and/or condition such newly formed droplets.

In some embodiments, the atomizer also comprises liquid and gas reservoirs. The liquid and gas reservoirs act as common reservoirs for each of the atomizing nozzles, receiving the supplies of liquid and gas respectively and providing liquid or gas to the atomizing nozzles.

Alternatively, each of the atomizing nozzles of an atomizer of the present invention is provided with individual liquid and/or gas reservoirs. According to this embodiment, gas and/or liquid flow to each atomizing nozzle may be individually controlled. Thus, a variety of liquid feedstocks may be fed to the individual atomizing nozzles in order to provide resultant dried powders with a variety of characteristics.

According to another aspect of the invention, the atomizer is provided with a plurality of different feedstocks, thereby providing a single step particle formation and blending process.

According to another aspect, the atomizer is provided with independent control of multiple atomization streams thereby enabling a wide degree of control over particle morphologies, particle sizes, and particle-size distributions.

According to another aspect, the present invention is directed to powder batches including coated particles and uniform powder blends of at least two discrete particle populations.

According to another aspect, the present invention is directed to a powder batch for a combination asthma therapy including a corticosteroid and a beta agonist wherein the powder batch is produced in a single step.

According to one embodiment, a pilot scale drying process is duplicated for commercial scale applications at 10 fold or greater throughput compared to pilot scale. As used herein, a commercial scale process refers to a spray drying process using a feedstock throughput of at least 500 ml/min. While this embodiment is useful in successfully duplicating performance characteristics at larger commercial scales, it is to be understood that the present invention is not limited to such high throughputs and may be practiced on smaller scales, for example at throughputs of less than 500 ml/min or less than 100 ml/min.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral and follows a hyphen to denote one of multiple similar components. When reference is made to a reference numeral without specification to an existing sublabel, it is intended to refer to all such multiple similar components.

DETAILED DESCRIPTION OF THE INVENTION

1. Introduction

Figure 1:
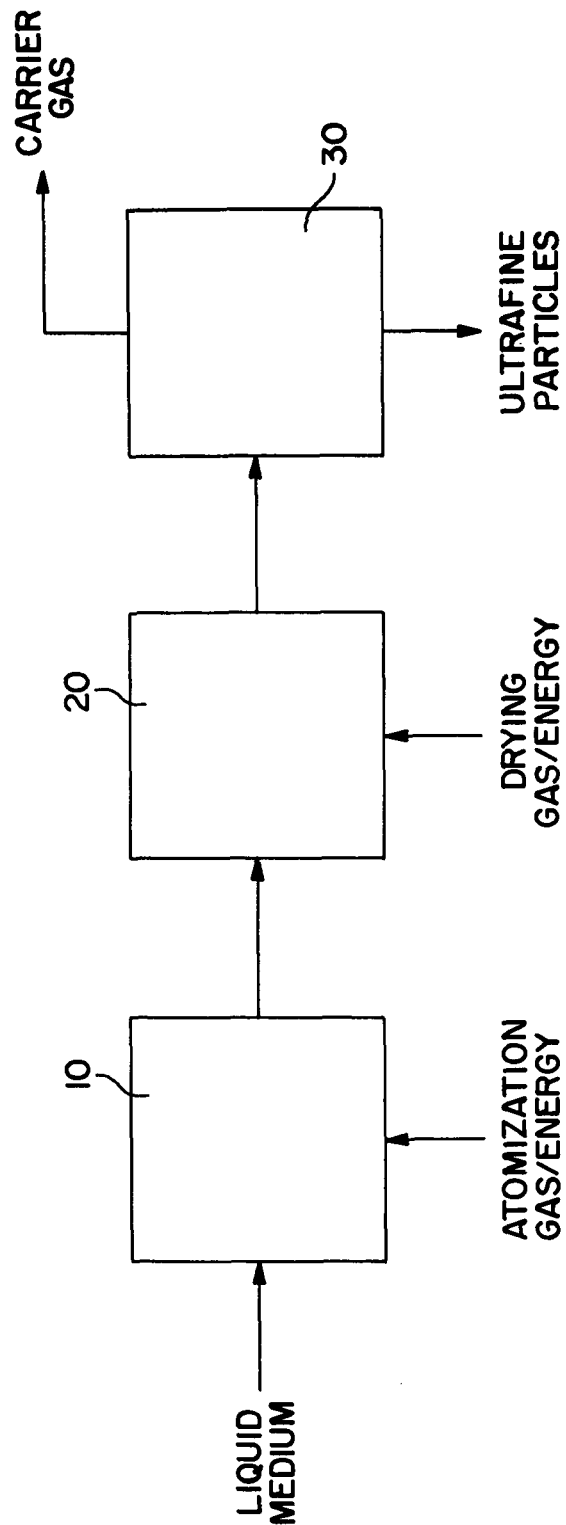
FIG. 1 is a block diagram illustrating primary unit operations of a commercial spray-drying process.

Embodiments of the present invention relate to methods and apparatuses suitable for commercial-scale preparation of dry powders. In particular, embodiments are suitable for preparing ultrafine dry powder of active agents particularly suited for pulmonary delivery to patients for a variety of therapeutic and clinical purposes. One aspect of the invention relates to control of powder characteristics that enhance the use of the powders for the intended purposes.

"Active agent" as described herein includes an agent, drug, compound, composition of matter or mixture thereof which provides some pharmacologic, often beneficial, effect. This includes feeds, feed supplements, nutrients, drugs, vaccines, vitamins, and other beneficial agents. As used herein, the terms further include any physiologically or pharmacologically active substance that produces a localized or systemic effect in a patient. The active agent that can be delivered includes antibiotics, antiviral agents, anepileptics, analgesics, anti-inflammatory agents and bronchodilators, and viruses and may be inorganic and organic compounds, including, without limitation, drugs which act on the peripheral nerves, adrenergic receptors, cholinergic receptors, the skeletal muscles, the cardiovascular system, smooth muscles, the blood circulatory system, synaptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, polysaccharides, steroids, hypnotics and sedatives, psychic energizers, tranquilizers, anticonvulsants, muscle relaxants, antiparkinson agents, analgesics, anti-inflammatories, muscle contractants, antimicrobials, antimalarials, hormonal agents including contraceptives, sympathomimetics, polypeptides, and proteins capable of eliciting physiological effects, diuretics, lipid regulating agents, antiandrogenic agents, antiparasitics, neoplastics, antineoplastics, hypoglycemics, nutritional agents and supplements, growth supplements, fats, antienteritis agents, electrolytes, vaccines and diagnostic agents.

Examples of active agents useful in this invention include but are not limited to insulin, calcitonin, erythropoietin (EPO), Factor VIII, Factor IX, ceredase, cerezyme, cyclosporine, granulocyte colony stimulating factor (GCSF), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-2, luteinizing hormone releasing hormone (LHRH), somatostatin, somatostatin analogs including octreotide, vasopressin analog, follicle stimulating hormone (FSH), insulin-like growth factor, insulintropin, interleukin-1 receptor antagonist, interleukin-3, interleukin-4, interleukin-6, macrophage colony stimulating factor (M-CSF), nerve growth factor, parathyroid hormone (PTH), thymosin alpha 1, IIb/IIIa inhibitor, alpha-1 antitrypsin, respiratory syncytial virus antibody, cystic fibrosis transmembrane regulator (CFTR) gene, deoxyribonuclease (Dnase), bactericidal/permeability increasing protein (BPI), anti-CMV antibody, interleukin-1 receptor, 13-cis retinoic acid, all trans-retinoic acid, sumatriptan, pentamidine isethionate, natural or synthetic lung surfactant, nicotine, albuterol sulfate, metaproterenol sulfate, amphotericin B, beclomethasone dipropionate, triamcinolone acetamide, budesonide acetonide, ipratropium bromide, flunisolide, fluticasone, cromolyn sodium, ergotamine tartrate and the analogues, agonists and antagonists of the above, ciprofloxacin, tobramicin, clarithromycin, gentamicin, and azithromicycin. Active agents may further comprise nucleic acids, present as bare nucleic acid molecules, viral vectors, associated viral particles, nucleic acids associated or incorporated within lipids or a lipid-containing material, plasmid DNA or RNA or other nucleic acid construction of a type suitable for transfection or transformation of cells, particularly cells of the alveolar regions of the lungs. The active agents may be in various forms, such as soluble and insoluble charged or uncharged molecules, components of molecular complexes or pharmacologically acceptable salts. The active agents may be naturally occurring molecules or they may be recombinantly produced, or they may be analogs of the naturally occurring or recombinantly produced active agents with one or more amino acids added or deleted. Further, the active agent may comprise live attenuated or killed viruses suitable for use as vaccines.

The active agent of the present invention may optionally be combined with pharmaceutical carriers or excipients. Such carriers or excipients may serve simply as bulking agents when it is desired to reduce the active agent concentration in the powder which is being delivered to a patient, or may be added to the active agent prior to processing for taste masking and/or to improve the stability and/or dispersability of the powder within a powder dispersion device. In other embodiments, the excipients may be delivered via the pulmonary route without an active agent, for example in clinical trials as a placebo. Such excipients include but are not limited to (a) carbohydrates, e.g., monosaccharides such as fructose, galactose, glucose, D-mannose, sorbose, and the like; disaccharides, such as lactose, trehalose, cellobiose, and the like; cyclodextrins, such as 2-hydroxypropyl-β-cyclodextrin; and polysaccharides, such as raffinose, maltodextrins, dextrans, and the like; (b) amino acids, such as glycine, arginine, aspartic acid, glutamic acid, cysteine, lysine, leucine, tri-leucine and the like; (c) organic salts prepared from organic acids and bases, such as sodium citrate, sodium ascorbate, magnesium gluconate, sodium gluconate, tromethamin hydrochloride, and the like; (d) peptides and proteins such as aspartame, human serum albumin, gelatin, and the like; (e) alditols, such as mannitol, xylitol, and the like; and (f) surfactants including fluorinated and nonfluorinated compounds such as saturated and unsaturated lipids, nonionic detergents, nonionic block copolymers, ionic surfactants and combinations thereof. A preferred group of excipients includes lactose, trehalose, raffinose, maltodextrins, glycine, leucine, tri-leucine, sodium citrate, human serum albumin, mannitol, and phospholipids from both natural and synthetic sources that preferably have a gel to liquid crystal phase transition greater than about 40° C. Preferred phospholipids are relatively long chain (i.e. $C_{16}$-$C_{22}$) saturated lipids and more preferably comprise saturated phospholipids, most preferably saturated phosphatidylcholines having acyl chain lengths of 16:0 or 18:0 (palmitoyl and stearoyl). Exemplary phospholipids include phosphoglycerides such as dipalmitoylphosphatidylcholine, disteroylphosphatidylcholine, diarachidoylphosphatidylcholine dibehenoylphosphatidylcholine, diphosphatidyl glycerol, short-chain phosphatidylcholines, long-chain saturated phosphatidylethanolamines, long-chain saturated phosphatidylserines, long-chain saturated phosphatidylglycerols, and long-chain saturated phosphatidylinositols.

As used herein, the term "emitted dose" or "ED" refers to an indication of the delivery of dry powder from a suitable inhaler device after a firing or dispersion event from a powder unit or reservoir. ED is defined as the ratio of the dose delivered by an inhaler device (described in detail below) to the nominal dose (i.e., the mass of powder per unit dose placed into a suitable inhaler device prior to firing). The ED is an experimentally-determined amount, and is typically determined using an in-vitro device set up which mimics patient dosing. To determine an ED value, a nominal dose of dry powder (as defined above) is placed into a suitable dry powder inhaler, which is then actuated, dispersing the powder. The resulting aerosol cloud is then drawn by vacuum from the device, where it is captured on a tared filter attached to the device mouthpiece. The amount of powder that reaches the filter constitutes the delivered dose. For example, for a 5 mg, dry powder-containing blister pack placed into an inhalation device, if dispersion of the powder results in the recovery of 4 mg of powder on a tared filter as described above, then the ED for the dry powder composition is: 4 mg (delivered dose)/5 mg (nominal dose)×100=80%. Compositions according to the present invention comprise emitted doses of at least 40%, preferably at least 60%, and most preferably at least 75%.

As used herein, the phrase "ultrafine dry powder" means a powder composition comprising a plurality of discrete, dry particles having the characteristics set forth below. In particular, the dry particles will have an average particle size below 50 μm, preferably below 10 μm, and most preferably below 5 μm, such as in the range from 0.4-5 μm. The average particle size of the powder is measured as mass median diameter (MMD) by conventional techniques. The powders are capable of being readily dispersed in an inhalation device and subsequently inhaled by a patient so that the particles are able to penetrate into the alveolar regions of the lungs.

The ultrafine dry powder compositions produced by embodiments of the invention may have particle size distributions that enable them to target the alveolar region of the lung for pulmonary delivery of systemically acting proteins. Such compositions advantageously may be incorporated into unit dosage and other forms without further size classification. In one embodiment, the ultrafine dry powders have a size distribution where at least 90% of the powder by weight comprises particles having an average size in the range from 0.1 μm to 7 μm, with preferably at least 95% being in the range from 0.4 μm to 5 μm. Additionally, in this embodiment, it is desirable that the particle size distribution avoid having an excess amount of particles with very small average diameters, i.e., below 0.4 μm or larger diameters, i.e. above 10 μm.

As used herein, the term "dry" means that the particles of the powder have a moisture content such that the powder is physically and chemically stable in storage at room temperature and is readily dispersible in an inhalation device to form an aerosol. In certain embodiments, the moisture content of the particles is below 10% water by weight. In specific embodiments, the moisture content may be below 5% by weight, below 3% by weight, below 2% by weight, or even below about 1% by weight or lower. The moisture content will usually be controlled by the drying conditions, as described in more detail below.

As used herein, the term "mass median aerodynamic diameter" ("MMAD") is a measure of the aerodynamic size of a dispersed aerosol particle. The aerodynamic diameter is used to describe an aerosolized particle in terms of its settling behavior, and is the diameter of a unit density sphere having the same settling velocity, generally in air, as the particle in question. The aerodynamic diameter encompasses particle shape, density, and physical size of a particle. MMAD refers to the midpoint or median of the aerodynamic particle size distribution of an aerosolized collection of particles determined by cascade impaction. The ultrafine dry powders of the present invention preferably comprise an MMAD within 1-5 microns.

Embodiments of the invention permit accurate and reproducible control of the spray-dryer atomizer droplet size distribution, which results in the production of spray dried particles having narrow particle-size distributions. In one such embodiment, particular atomizer spray characteristics are provided that result in the production of particles suitable for pulmonary administration. The spray-dryer atomizer is provided to produce a spray of droplets having a median diameter less than 20 µm. In particular embodiments, the median diameter of droplets may be less than 10 µm.

According to another embodiment, the atomizer droplet size distribution is controlled to produce a multimodal collection of particles with a predetermined particle size and particle-size distribution. According to this embodiment, multiple populations of particles having distinct particle size distributions are provided. These multiple populations may be formed from the same or different feed stock formulations. For example, a multimodal distribution according to this embodiment may comprise active agent containing particles having a first MMAD in the respirable range and a second population of particles without any active agent and having a MMAD within or outside the respirable range. Alternatively, the second population of particles may comprise the same or a different active agent than the first population, or may consist of pharmaceutically acceptable excipients without an active agent. Additionally, multimodal distributions according to this invention are not limited to only two distinct populations, but may include as many distinct populations as desired.

Certain additional aspects of desirable powder properties, as well as certain aspects of spray-drying systems, are described in the various patents and patent publications previously cited above.

2. Spray Drying System

Referring now to FIG. 1, spray-drying processes for preparing dispersible dry powders of active agents comprise an atomization operation 10 that produces droplets of a liquid medium, which are subsequently dried in a drying operation 20. Drying operation 20 may be a single drying chamber or a multi-stage operation. Drying of the liquid droplets results in formation of the discrete particles that form the dry powder compositions which are then collected in a separation operation 30. Each of these unit operations is described in greater detail below.

The atomization process 10 increases the surface area of the starting liquid. This requires an increase in the surface energy of the liquid, the magnitude of which is directly proportional to the area increase, which in turn, is inversely proportional to the square of the diameter of the droplets. The source of this energy increase results from the use of a multi-nozzle two-fluid atomizer where the liquid medium is delivered through the multiple nozzles concurrently with high pressure gas streams.

The atomization gas is usually air that has been filtered or otherwise cleaned to remove particulates and other contaminants. Alternatively, other gases, such as nitrogen, may be used. The atomization gas is pressurized for delivery through the multi-nozzle atomizer, typically to a pressure above 25 lb/in$^2$, preferably being above 50 lb/in$^2$. The atomization conditions, including atomization gas flow rate, atomization gas pressure, liquid flow rate, and the like, are controlled to produce liquid droplets having an average diameter below 20 or 10 µm, depending on the embodiment, as measured by phase Doppler particle analysis (PDPA), such as with a Phase Doppler Particle Size Analyzer (Aerometrics). In some embodiments, the atomized droplets have an average diameter in the range from 5 µm to 11 µm, and in one embodiment from 6 µm to 8 µm. In a preferred embodiment, the gas:liquid mass flow ratio may be maintained above 2, preferably in the range from 3 to 15.

The feedstock may be a solution, suspension, colloidal system, or other dispersion of a pharmaceutical in a suitable liquid carrier. In one embodiment, the active agent is present as a solution in a liquid solvent and the liquid carrier is water. It is possible, however, to employ other liquid solvents, such as organic liquids, ethanol, and the like. The total dissolved solids, including the macromolecule and other carriers, excipients, etc., that may be present in the final dried particle, may be present at a wide range of concentrations, typically being present at from 0.1% by weight to 10% by weight. Usually, however, it will be desirable to maximize the solids concentration that produces particles in the inhalation size range and has the desired dispersibility characteristics, typically the solids concentration ranges from 0.5% to 10%, more narrowly from 1.0% to 5%. It will thus be understood that the term "feedstock" as used herein is used broadly and encompasses mixtures such as solutions, slurries, suspensions, emulsions, microemulsions, multiple emulsions, and reverse emulsions. Feedstocks containing relatively low concentrations of the active agent will result in dried particulates having relatively small diameters as described in more detail below. Suitable feedstock preparation for use according to the methods of the present invention are disclosed in, for example, WO 96/32149, WO 99/16419 and WO 01/85136 and in U.S. Pat. Nos. 5,976,574, 5,985,248, 6,001,336, 6,051,256, 6,077,543, and 6,423,344 which have been previously cited above.

The drying operation 20 is performed next to evaporate liquid from the droplets produced by the atomization operation 10. Usually, the drying includes introducing energy to the droplets, typically by mixing the droplets with a heated gas which causes evaporation of the water or other liquid medium. In one embodiment, the mixing is done in a spray dryer or equivalent chamber where a heated gas stream has been introduced. The heated gas stream may flow concurrently with the atomized liquid, but it would also be possible to employ counter-current flow, cross-current flow, or other flow patterns. It is also possible to perform the drying operation in multiple stages as described in more detail in WO 01/00312 cited above.

The drying operation may be controlled to provide dried particles having particular characteristics, such as a rugosity above 2 as described in U.S. Pat. No. 6,051,256 cited above. Rugosity is a measure of surface convolution, with a higher number indicating a higher degree of surface irregularity. Without intending to limit the scope of the present invention in any way, it is believed that the increase in surface irregularity as measured by rugosity results in a decrease in cohesiveness between adjacent particles. Alternatively, the drying operation may be controlled to produce particles having smooth or substantially smooth surfaces.

Thereafter, the drying rate should be sufficiently rapid so that the moisture is removed through the exterior layer of material, resulting in collapse and convolution of the outer layer to provide a highly irregular outer surface. The drying rate may be controlled based on a number of variables, including the droplet size distribution, the inlet temperature of the gas stream, the outlet temperature of the gas stream, the inlet temperature of the liquid droplets, and the manner in which the atomized spray and hot drying gas are mixed. In one embodiment, the drying gas stream has an inlet temperature of at least 90° C., and may be at least 120° C., at least 135° C., at least 145° C., and may often be over 175° C., or even as high as 200° C., depending on the active agent being dried. At least in part, the inlet temperature of the heated gas drying stream depends on the lability of the active agent being treated. The outlet temperature is usually in the range of about 60-100° C. The drying gas is usually air that has been filtered or otherwise treated to remove particulates and other contaminants. The air is moved through the system using conventional blowers or compressors. The drying gas may, alternatively, be nitrogen or other non-oxidizing gas suitable for safe use with organic solvents other than water.

The separation operation 30 is selected to achieve very high efficiency collection of the ultrafine particles produced by the drying operation 20. Conventional separation operations may be used, although in some cases they could be modified to assure collection of submicron particles. In an exemplary embodiment, separation is achieved using a filter medium such as a membrane medium (bag filter), a sintered metal fiber filter, or the like. Alternatively, separation may be achieved using cyclone separators. The separation operation should achieve collection of at least 80% of all particles above 1 µm in average particle size, and in some embodiments collects more than 85%, more than 90%, or even more then 95% of such particles.

In some cases, a cyclone separator can be used to separate very fine particles, e.g. of about 0.1 µm diameter, from the final collected particles. The cyclone operating parameters can be selected to provide an approximate cutoff where particles above about 0.1 µm are collected while particles below about 0.1 µm are carried over in the overhead exhaust. The presence of particles below about 0.1 µm in pulmonary powder is generally undesirable since they will usually not deposit in the alveolar regions of the lungs, but instead will be exhaled.

Figure 2:
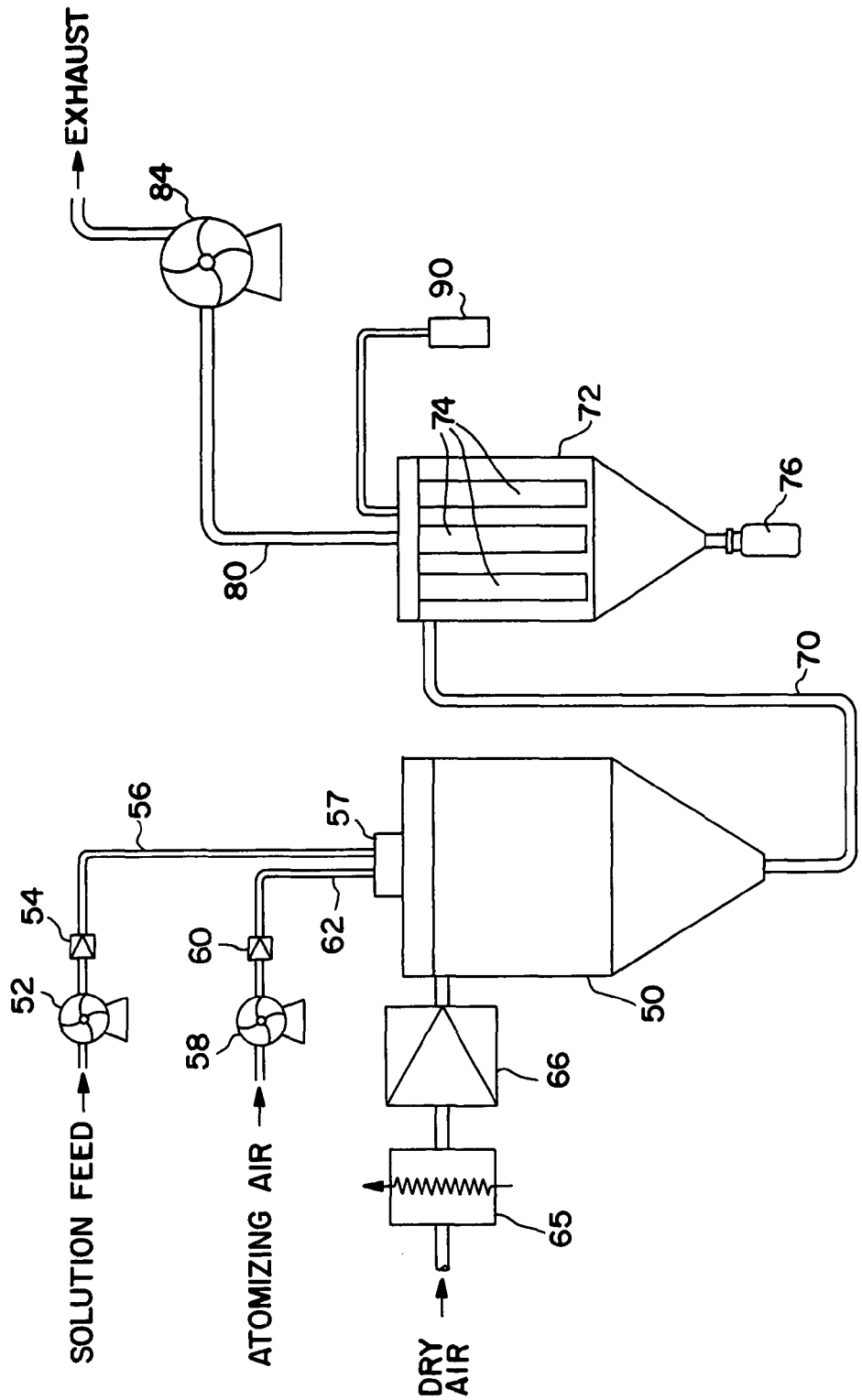
FIG. 2 is a detailed schematic diagram illustrating a spray-drying system suitable for use with embodiments of the invention.

Referring now to FIG. 2, an exemplary spray-dryer system is described. The system includes a spray dryer 50, which may be a commercial spray dryer such as those available from suppliers such as Buchi, Niro, APV, Yamato Chemical Company, Okawara Kakoki Company, and others. The spray dryer 50 is provided with a feedstock as described above through a supply pump 52, filter 54, and supply line 56. The supply line 56 is connected to a multi-nozzle two-fluid atomizer 57, as described below in connection with FIGS. 3A and 3B. Atomizing air is supplied from a compressor 58, a filter 60, and line 62 to the atomizer 57. Drying air is also provided to the spray dryer 50 through a heater 65 and a filter 66.

Dried particles from the spray dryer 50 are carried by the air flow through conduit 70 to a filter housing 72. The filter housing 72 includes a plurality of internal filter elements 74, which may be bag filters or sintered metal fiber filters, such as sintered stainless steel fiber filters of the type described in Smale, Manufacturing Chemist, p. 29, April 1992. Alternative filter media comprise bag filters, cloth filters, and cartridge filters. In all cases, the gas stream carrying the dried particles flows into the shell of separator housing 72, and the carrier gas passes through the filter elements 74. Passage of the dried particles, however, is blocked by the filter elements, and the dried particles fall by gravity to the bottom of the housing 72 where they are collected in a particle collection canister 76. The canister 76 may periodically be removed and replaced, and the dry powder in the canister 76 used for packaging in unit dosage or other forms. The carrier gas passes out from the top of the separator housing 72 through line 80 and an exhaust fan 84. The filters 82 collect any particles that may inadvertently pass through the filter media 74. A source 90 of high-pressure gas is provided for periodically producing a pulsed flow of counter-current air through the filter media 74. Such pulsed air flow in the reverse direction dislodges particles that adhere to the inlet side of the filter medium to prevent caking.

3. Multi-Nozzle Atomizer

Figure 3:
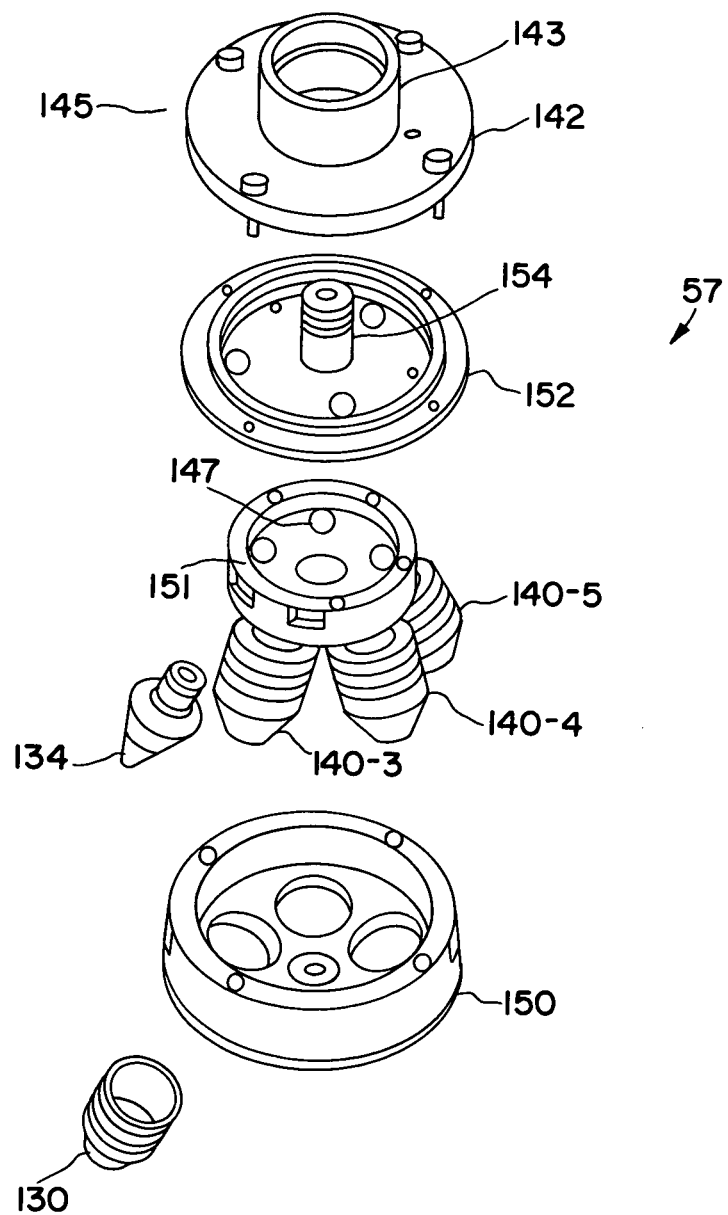
FIG. 3 is an exploded view of an embodiment of a multi-nozzle atomizer according to the invention.
Figure 4:
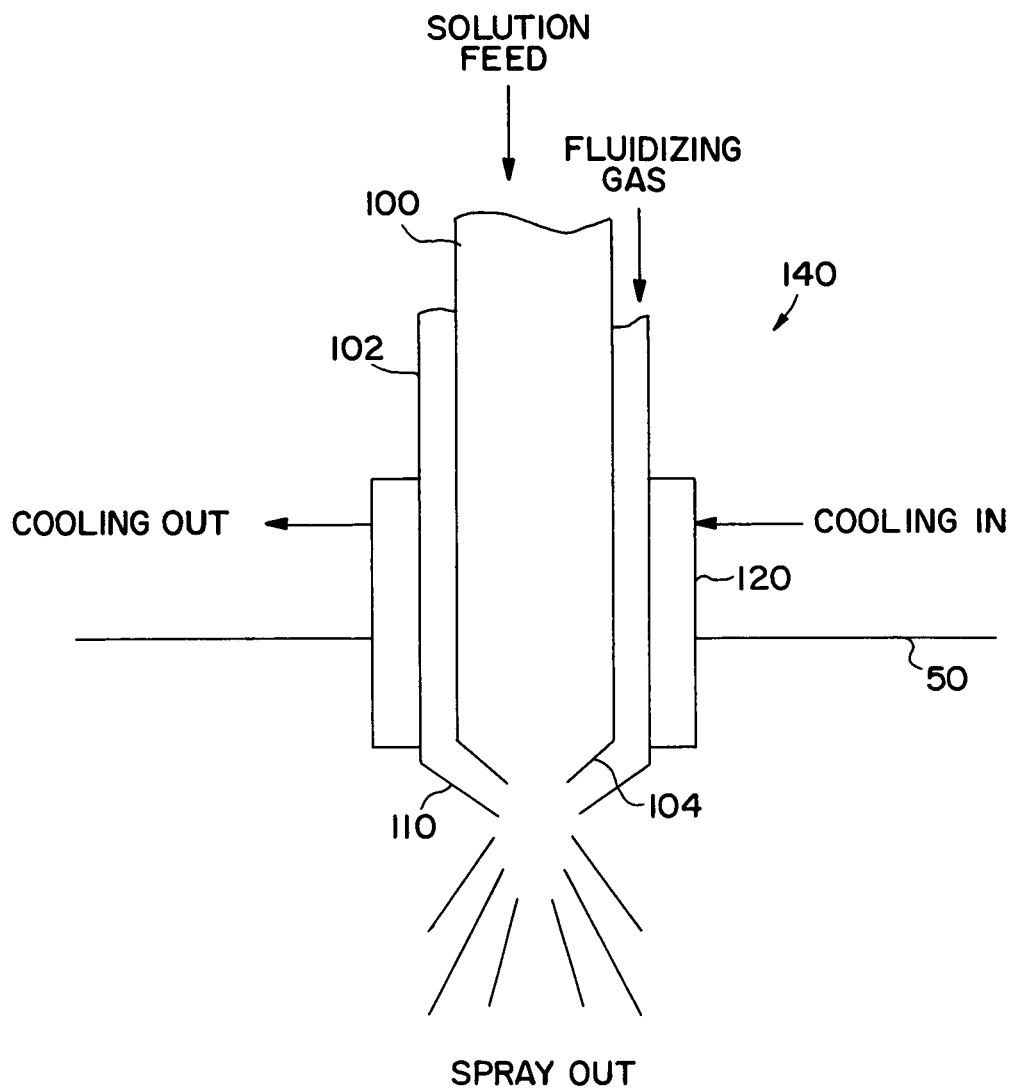
FIG. 4 is a schematic illustration of the operation of an individual nozzle of a multi-nozzle atomizer.

With laboratory and pilot-plant scale spray dryers, it is possible to achieve the desired atomizer performance, for both droplet size and droplet size distribution, for the relatively low liquid throughputs used. In scaling up to commercial plant scale, this performance can be maintained in accordance with embodiments of the invention by using a multi-nozzle atomizer. One such embodiment is illustrated in FIG. 3 for a multi-nozzle sonic gas-assisted liquid atomizer, although other types of atomizers, such as rotary and ultrasonic atomizers, may also be adapted to use the multi-nozzle configuration. FIG. 3 provides an exploded view showing individual components and FIG. 4 shows a schematic representation of the operation of an individual nozzle. The discussion below refers generally to both figures in describing the structure.

The atomizer 57 includes an array of twin-fluid nozzles 140 coupled together in a single housing 150. Each nozzle 140 is preferably releasably attached to the housing so that they may be readily removed to facilitate cleaning. FIG. 3 shows an array of five such nozzles 140, although different numbers of nozzles 140 may alternatively be used. Each nozzle 140, depicted schematically in FIG. 4, comprises a liquid nozzle 134 and a gas nozzle 130. Each of the liquid nozzles 134 is adapted to be mounted on a support member 151, both the support member 151 and liquid nozzles 134 including conduits 147 to permit a flow of feedstock from a common reservoir (not shown) through the liquid nozzles 134. The housing 150 includes a plurality of openings through which the nozzles protrude when the housing 150 is mounted to the support member 151. Each gas nozzle 130 is configured coaxially as a cap surrounding one of the liquid nozzles 134 to permit a flow of gas from a common gas reservoir (not shown).

The nozzles 140 are tilted at an angle with respect to the atomizer centerline to limit interaction of plumes from the individual nozzles 140. The tilt angle may be between 0° and 180°, preferably between 10° and 40°. In one embodiment, the tilt angle is between 15° and 25°. Such a tilt angle permits the atomizer 57 additionally to include an optional center gas nozzle. The optional center nozzle is adapted to provide an additional gas flow to the spray dryer in order to prevent the multiple spray cones from collapsing on one another, resulting in droplet coalescence and increased particle sizes.

The supplemental nozzle may be adapted to disperse a gas and/or liquid. For example, the supplemental nozzle may provide a separate gas stream at a temperature different from the atomizing nozzles to thermally condition the droplets dispersed from the atomizing nozzles at the near nozzle regions. Alternatively, the supplemental nozzle may disperse a gas and/or liquid stream of an active agent or excipient to form a film around the droplets exiting the atomizing nozzles. When dried, this film forms a dried coating around the dried droplet core. Leucine vapor is one example of a gas stream dispersed from the supplemental nozzle to impart desired modifications to the particles formed by the spray drying process of the present invention. Other excipients are known in the art as disclosed in the various patents cited above.

The support member 151 is coupled with ring 152, which includes channel 154 for connecting the feedstock reservoir and gas reservoir with the flow line 56. The flow line 56 includes inner and outer conduits so that the feedstock and fluidizing gas are provided to their respective reservoirs for expulsion through the nozzles 140. Ring 152 is further adapted for mounting with the top plate 145. The top plate includes a flange portion 142 that acts to enclose the atomizer 57 when assembled and includes an open column 143. The open column 143 is sized and shaped for engagement with an atomizer connection in a commercial-scale spray dryer. As configured, the open column 143 permits the flow line 56 to be coupled with the channel 154 to the common solution and gas reservoirs.

Referring now to FIG. 4, the detailed operation of each of the two-fluid nozzles 140 comprised by the atomizer 57 is illustrated. Each nozzle 140 includes an inner conduit 100 and outer conduit 102 that are respectively connected with the common solution reservoir and common gas reservoir. The inner conduit 100 carries the solution feed and terminates in an orifice 104 having a diameter in the range from 0.015 in. to 0.075 in., perhaps from 0.025 to 0.05 in. depending on the liquid flow rate. The outer conduit 102 is disposed coaxially about the inner conduit 100 and carries the atomizing gas from line 62. Conduit 100 terminates in an orifice 110 that is concentric about the orifice 104 of conduit 100. The diameter of orifice 110 is typically larger than that of orifice 104, usually having a cross-sectional area sufficient to produce the desired mass flow rate of air with the desired upstream pressure.

Optionally, a cooling jacket 120 may be provided about each nozzle 140 to maintain a relatively low temperature of the solution feed when the solution feed enters the spray dryer 50. The cooling jacket 120 typically carries cooling water at a temperature and in an amount sufficient to maintain the solution feed temperature below a level at which the active agent might be degraded, usually from 4° C. to 45° C. Cooling is generally necessary only with heat-sensitive active agents. Higher solution feed temperatures result in lower viscosity, where the lower viscosity can reduce the droplet size formed by the atomization operation.

Thus, in operation, the liquid to be atomized is provided from the flow line 56 via channel 154. The liquid is then directed to each of the individual liquid nozzles 134. The fluidizing gas is fed to the gas nozzles 130, which encompass their partner liquid nozzles 134. With the dimensions set forth above, the multi-nozzle atomizer 57 is capable of producing, at commercial scales, liquid sprays with volume mean diameters less than 20 µm at liquid flow rates up to 1 L/min. In certain instances, at such liquid flow rates, the volume mean diameters may be less than 10 µm or even less than 5 µm.

For example, when individual liquid feeds are provided to each atomizer nozzle, the solids concentration can be varied among the feed stock formulations delivered to each of the nozzles of the structural assembly. Particle size of the dried particles is a function of the initial droplet diameter and feedstock solution concentration, among other factors. Feed stock formulations comprising lower solids concentrations will result in dried particulates having a smaller particle size compared to the other feed stocks. Thus, multimodal particle size distributions can be controlled by altering the solution concentration of a desired active agent in the various feedstocks individually supplied to the atomizer nozzles. Typical feed stock solids concentrations are within the range 0.1-10% by weight, preferably 1-5% by weight and may be selected in order to provide the desired particle size and size distribution, with lower solids content generally providing smaller particle sizes.

Alternatively, different gas circuits could be provided to each of the nozzles of the structural assembly in order to provide each nozzle with different gases and/or different operating parameters, such as flow rates and pressures, in order to alter droplet size and distribution and hence create dried particulates of different particles sizes and particle size distributions.

In addition to altering particle size and particle size distributions through control of liquid and gas feeds to individual nozzles, the provision of individual liquid feeds to individual atomizer nozzles also enables the simultaneous production of a particulate batch comprising particles of varying compositions. For example, batches comprising individual particles containing different active agents can be produced by providing at least one liquid feed comprising a first active agent to at least one atomizing nozzle while also providing at least one other atomizing nozzle with a liquid feed comprising a second active agent. Controlling individual liquid feeds to specific atomizing nozzles is not limited to providing multiple active agents. For example, at least one liquid feed may be provided with a pharmaceutically acceptable excipient, as known in the art as seen in the patents cited above, so as to provide a particulate batch wherein at least some of the particles are free of any pharmaceutically active agent. Suitable excipients are preferably a mono-, di-, or polysaccharide, a sugar alcohol, or another polyol. Suitable excipients include, for example, lactose, glucose, raffinose, melezitose, lactitol, mannitol, malitol, trehalose, sucrose, and starch. Lactose is an example of one such excipient that may be used in a liquid feed absent active agent. It is to be understood that these excipients may also be used together in the feedstock comprising an active agent. According to this embodiment, an aqueous feedstock and a feedstock comprising an organic solvent can be spray dried at the same time.

According to this embodiment of the invention, a powder blend of at least two active agents may be provided in a single step. A preferred combination according to the present invention is directed to asthma treatments wherein two or more active agents selected from corticosteroids, short or long acting beta agonists, and bronchodilating agents are used for the combination therapy. Preferred corticosteroids include fluticasone, beclomethasone, budesonide, cortisone, dexamethasone, flunisolide, hydrocortisone, prednisoline, prednisone, triamcinolone, ciclesonide, rofleponide, mometasone, and pharmaceutically acceptable salts, hydrates and esters thereof. Preferred beta agonists include albuterol, tolubuterol, fenoterol, terbutaline, formoterol, salmeterol, and pharmaceutically acceptable salts and esters thereof. Preferred additional bronchodilators include ipratropium and pharmaceutically acceptable salts, esters, hydrates, solvates, and isomers thereof. Such combination therapies are known in the art, for example as disclosed in WO 99/64014, and U.S. Pat. No. 5,674,860, which are hereby incorporated in their entirety by reference. A particularly preferred combination of the present invention is budesonide and formoterol fumarate.

According to this embodiment, the particles produced according to the present invention may comprise a core particle coated by a discrete continuous or discontinuous layer. Such coating may be provided by directing the spray plume of one nozzle such that it contacts that of at least one additional nozzle. Alternatively, a central spray nozzle as discussed above may be utilized to direct a spray of the coating material into contact with at least one additional spray. In either embodiment, the target substance making up the core particle and the target substance comprising the coating layer are provided in separate atomization circuits of the atomization nozzle. For example, a bronchodilator may be separately provided in one feedstock and coated onto a core particle comprising a beta agonist provided via a second feedstock. It is to be understood that this embodiment is not to be limited to providing multiple active agents nor particle for pulmonary administration. For example, the target substance comprising the coating layer may be a taste masking agent to improve the flavor profile of an orally administered active agent provided in the form of, for example, a particle for oral administration in a capsule or via suspension, a lozenge, or in tablet form. Such taste masking excipients include, for example, a polyol such as mannitol, sorbitol, sucrose, and lactitol, and biodegradable polymers such as cellulose derivatives, preferably ethyl cellulose. Other taste masking agents suitable for use with the present invention are disclosed in WO 98/47493, hereby incorporated in its entirety by reference.

Alternatively, the two or more active agents may be provided as a mixture in a single feedstock. Depending on the relative dosages of the two or more active agents, the resultant spray dried particles may comprise a substantially homogeneous particle or, if one active agent is to be administered at a substantially lesser dosage than the other, the resultant particles may comprise a core of the lower dose active agent substantially coated by the larger dose active agent. According to a preferred embodiment directed to asthma treatments, a higher proportion of active agent comprises a corticosteroid and a lower proportion of active agent comprises a beta agonist or other bronchodilator. The relative dosage of the selected active agents may be readily determined by one of ordinary skill in the art.

In yet another alternative of this embodiment, a powder blend comprising a particle population of a first composition and at least a second particle population of a second composition may be produced in a single step. Such powder blends are produced by providing separate feedstocks to individual nozzles of the atomizer. The compositions used to produce the powder blends may comprise different active agents. For example, a first feedstock comprising a corticosteroid is provided to one or more individual nozzles and a second feedstock comprising a beta agonist or other bronchodilator is provided to at least one of the remaining nozzles of the multi-head atomizer assembly. Alternatively, the first composition may comprise an active agent and the second composition may comprise excipient only, preferably lactose.

According to this embodiment, the present invention provides a single step process to produce substantially uniform powder blends comprising particles of at least two different compositions. According to a preferred embodiment, the powder blend comprises ultrafine dry powders comprising a uniformity index of within 25%, preferably within 15%, on a mass/mass basis. The uniformity index is the consistency of the mass ratio of the constituent components of the powder blend throughout a collected powder batch. The ability of the present invention to provide such uniform powder blends, particularly for ultrafine dry powders for respiratory administration, is particularly unexpected.

Figure 5:
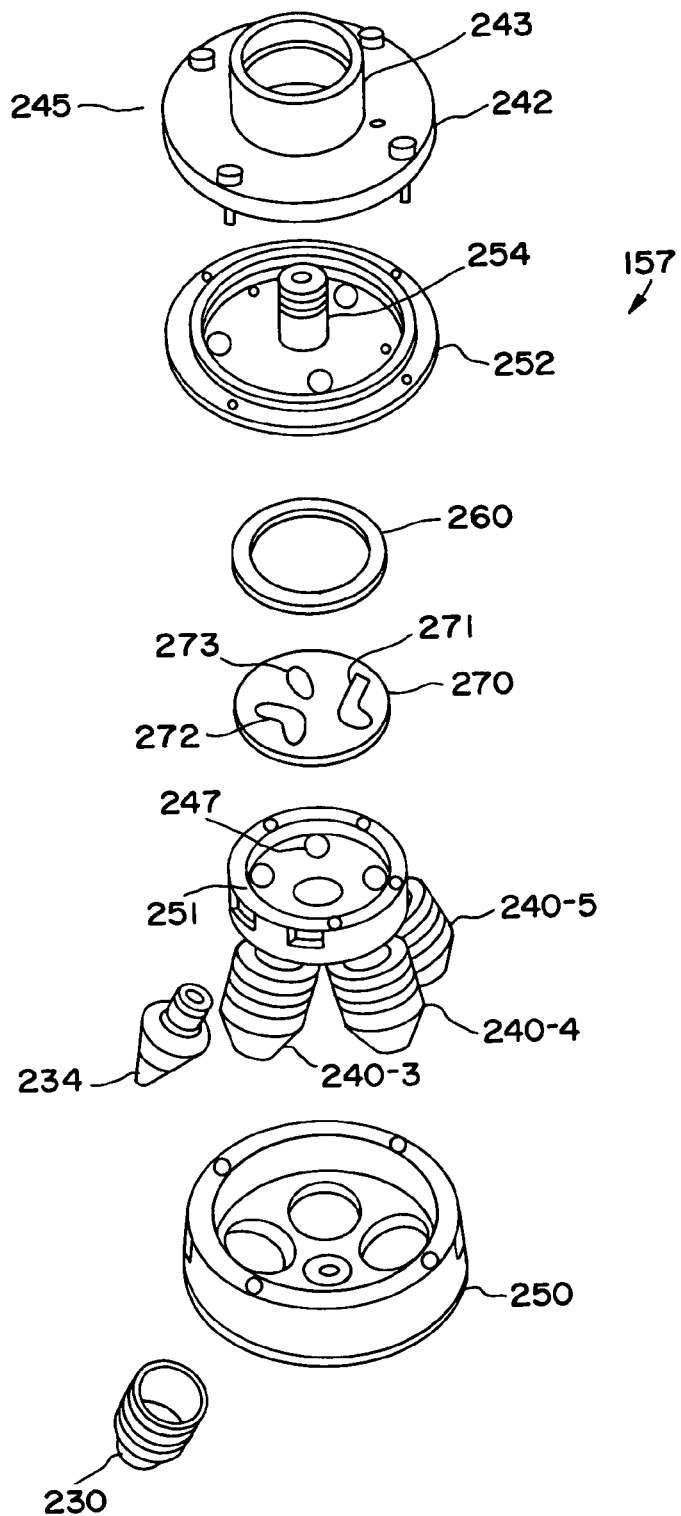
FIG. 5 is an exploded view of an embodiment of a multi-nozzle atomizer with individual atomization circuits.

An example of a nozzle accommodating individual control of multiple liquid feedstocks is depicted in FIG. 5. As seen in FIG. 5, nozzle 157 is substantially the same as that of FIG. 3b. In order to control the distribution of the various feedstocks to the nozzles, reservoir inlet 260 and manifolding gasket 270 are provided. According to this embodiment, two nozzles have been isolated by opening 271 of manifolding gasket 270 to provide a first feedstock to the associated nozzles, a second set of two nozzles has been isolated by opening 272 of manifolding gasket 270 to provide a second feedstock to the nozzles associated thereto, and a single nozzle has been isolated by opening 273 of manifolding gasket 270 to provide an additional nozzle for either of the first or second feedstocks, or to provide for a third feedstock to be atomized. One of ordinary skill in the art can modify manifolding gasket in order to provide for a desired number and/or orientation of atomization circuits.

The invention is further illustrated in greater detail with the aid of the following examples without being restricted thereto:

Example 1

The blending capabilities according to one aspect of the invention was investigated. Two aqueous solutions were spray dried in roughly equal proportions using the atomizer of the present invention in conjunction with a Niro (Mobile Minor) spray dryer. The two solutions consisted of: 1) monobasic sodium phosphate with leucine in a 1:1 ratio at 1% total solids concentration, and 2) dibasic sodium phosphate with leucine in a 1:1 ratio at 1% total solids concentration. This phosphate buffer system was selected due to its favorable pH stability and well-known pH vs. mixture ratio relationship. Two peristaltic pumps were provided to deliver the solutions to the atomizer circuits, with one pump feeding three circuits (three nozzles) and the second pump feeding the remaining two circuits (nozzles).

The solutions were spray dried with the atomizer under the following conditions:

| SPRAY DRYER RUN CONDITIONS | |
| --- | --- |
| Solution 1 (NaH$_2$PO$_4$-Leu) Feed Rate: | 30.1 ml/min (3 nozzles) |
| Solution 2 (Na$_2$HPO$_4$-Leu) Feed Rate: | 28.5 ml/min (2 nozzles) |
| Atomizer Gas Pressure and Flow Rate: (SCFM = 0.582*psig + 7.239) | 40 psig, 30.5 SCFM |
| Solution 1 Air-to-Liquid Ratio (mass): | 20.7 |
| Solution 2 Air-to-Liquid Ratio (mass): | 14.5 |
| Total Dryer Flow Rate: | 104 SCFM |
| Dryer Inlet Temperature: | 190° C. |
| Dryer Outlet Temperature: | 73° C. |
| Cyclone Exhaust Temperature: | 64° C. |
| Run Time: | 80 minutes |

The resulting powder blend was sampled at various locations throughout the collector to determine the blend uniformity. The powder was carefully poured out of the collector into a plastic weighing boat in a four-tiered continuous line. Twelve sampling locations were selected within the powder bed and three replicates were taken at each of these twelve locations for a total of 36 samples. Each sample was obtained by capturing a small amount of powder (approximately 20 mg) with a spatula. Each individual powder sample was weighed and then transferred to a small vial where it was subsequently reconstituted to 1% concentration for pH testing.

pH measurements were made on each reconstituted powder mixture sample and compared with data from a calibration curve to determine the mixture ratio of the two constituents in the powder blend. A simple pH mixing assay was selected as the method of characterization for the degree of mixing or blend uniformity in the collected powder mixture. This method consisted of using a system of two solutions with a well-defined relationship between pH and solution mixture ratio (i.e. ratio of Solution 1 to Solution 2 by volume). A pH calibration curve was generated for these solutions in various mixture ratios by volume. Results of this calibration are shown below in Table 1 and graphically in FIG. 5. Based on the pH calibration curve for various mixture ratios, samples of the collected powder blend were reconstituted and pH measurements were then made to determine the degree of mixing.

Tables 2 and 3 contain the pH testing data from the 36 samples across the 12 powder bed locations as well as appropriate averages and statistics. The blend uniformity or homogeneity of the mixture is indicated by the variation in pH measurements across the 12 powder bed locations as well as across the three replicates at each location. Regardless of the absolute value of the pH, small sample-to-sample and location-to-location variations are indicative of a uniform blend. The absolute value of the pH measurements indicates the mixture ratio of the collected powder and is a direct indicator of whether there was preferential collection of one constituent over the other.

A comparison of the pH measurements across 36 powder samples over 12 locations within the collector yielded a location-to-location relative standard deviation of 0.2% and a total sample relative standard deviation of 0.2%, clearly indicating that the two powders were well-mixed. Moreover, the absolute value of the pH measurements in the collector was within 3% of the mixture ratio at which the two solutions were delivered to the dryer, indicating that there was no preferential particle collection.

Figure 6:
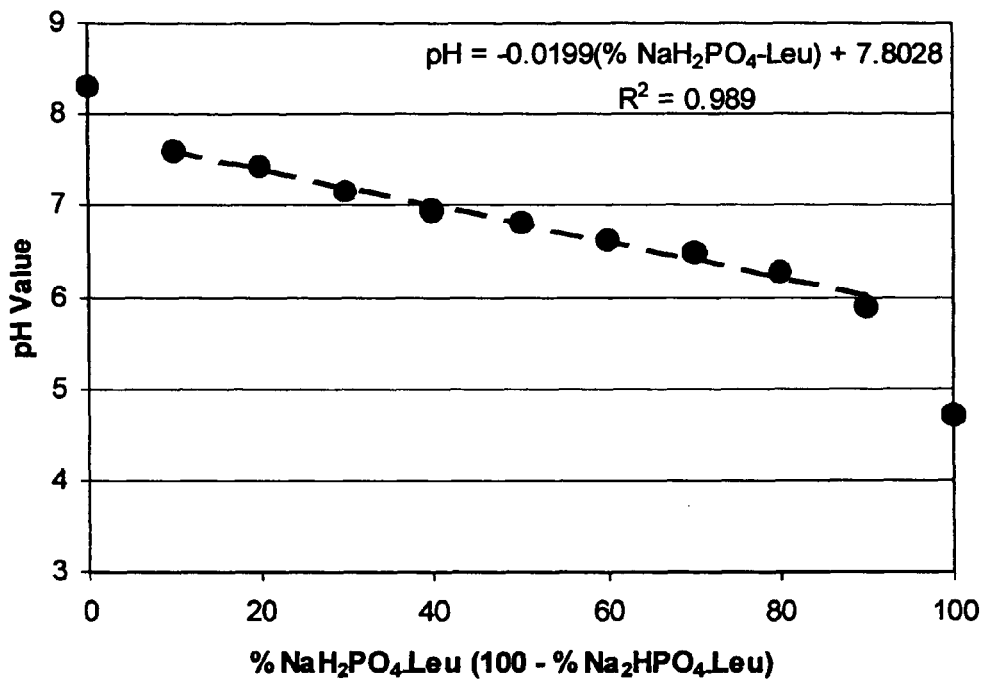
FIG. 6 depicts a calibration curve used in the determination of powder blend uniformity.
Figure 7:
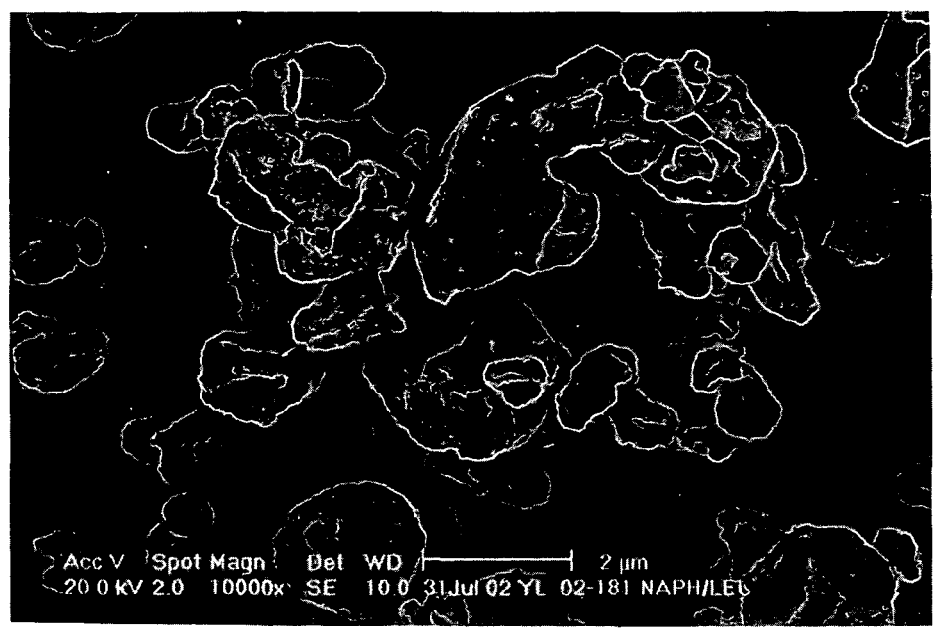
FIG. 7 are SEM images of powders produced according to the invention.

Scanning electron microscope (SEM) images of the powder mixture are depicted in FIG. 6 and particle size data obtained using a Sympatec laser diffraction particle sizing instrument is listed in Table 4.

TABLE 1 pH vs. Phosphate Mixture Ratio by Volume

| % NaPh-Leu | % Na$_2$Ph-Leu | Measured pH |
|---|---|---|
| 100 | 0 | 4.704 |
| 90 | 10 | 5.905 |
| 80 | 20 | 6.269 |
| 70 | 30 | 6.477 |
| 60 | 40 | 6.629 |
| 50 | 50 | 6.827 |
| 40 | 60 | 6.957 |
| 30 | 70 | 7.148 |
| 20 | 80 | 7.433 |
| 10 | 90 | 7.606 |
| 0 | 100 | 8.302 |

TABLE 2

Powder Bed pH Sampling Data

| | Powder Bed Location | | | | | | | | | | | |
|---|---|---|---|---|---|---|---|---|---|---|---|---|
| Measurement | 1 | 2 | 3 | 4 | 5 | 6 | 7 | 8 | 9 | 10 | 11 | 12 |
| 1 | 6.734 | 6.720 | 6.715 | 6.684 | 6.699 | 6.715 | 6.730 | 6.725 | 6.703 | 6.701 | 6.729 | 6.724 |
| 2 | 6.749 | 6.734 | 6.710 | 6.725 | 6.706 | 6.696 | 6.722 | 6.708 | 6.708 | 6.715 | 6.741 | 6.718 |
| 3 | 6.736 | 6.751 | 6.730 | 6.724 | 6.704 | 6.713 | 6.724 | 6.699 | 6.713 | 6.711 | 6.741 | 6.724 |
| Average pH | 6.740 | 6.735 | 6.718 | 6.711 | 6.703 | 6.708 | 6.725 | 6.711 | 6.708 | 6.709 | 6.737 | 6.722 |
| STDEV | 0.008 | 0.016 | 0.010 | 0.023 | 0.004 | 0.010 | 0.004 | 0.013 | 0.005 | 0.007 | 0.007 | 0.003 |
| RSTDEV | 0.1% | 0.2% | 0.2% | 0.3% | 0.1% | 0.2% | 0.1% | 0.2% | 0.1% | 0.1% | 0.1% | 0.1% |

TABLE 3

Location to Location pH Statistics

| | |
|---|---|
| Average of All Samples | 6.719 |
| All Samples STDEV | 0.015 |
| All Samples RSTDEV | 0.2% |
| STDEV Locations 1-12 | 0.013 |
| RSTDEV Locations 1-12 | 0.2% |

TABLE 4

Powder Blend Particle Size Data (Sympatec)

| Test | x10 (μm) | x16 (μm) | x50 (μm) | x84 (μm) | x90 (μm) | x99 (μm) | Sv (m$^2$/cm$^3$) | VMD (μm) |
|---|---|---|---|---|---|---|---|---|
| 1 | 0.77 | 0.91 | 1.60 | 2.70 | 3.10 | 5.51 | 4.37 | 1.82 |
| 2 | 0.78 | 0.91 | 1.59 | 2.71 | 3.14 | 5.74 | 4.35 | 1.83 |
| 3 | 0.79 | 0.92 | 1.60 | 2.70 | 3.12 | 5.33 | 4.33 | 1.82 |
| Average | 0.78 | 0.91 | 1.60 | 2.70 | 3.12 | 5.53 | 4.35 | 1.82 |

Example 2

Three spray drying runs were performed using various feedstocks of a raffinose solution, raffinose and leucine solutions provided from separate nozzles, and a raffinose/leucine mixture. The three runs are further described below:

Spray Drying Run Number 87-1
  Solution 1: Raffinose
    Solids Content (weight percent): 10%
    Number of Nozzles: 2
    Total Flow Rate: 30 ml/min (15 ml/min per nozzle)
  Solution 2: Water
    Solids Content (weight percent): n/a
    Number of Nozzles: 3
    Total Flow Rate: 30 ml/min (10 ml/min per nozzle)
  Dryer Initial Condition: Clean
  Atomizer Pressure: 40 psig
  Total Dryer Flow Rate: 110 SCFM
  Dryer Inlet Temperature: 195° C.
  Dryer Outlet Temperature: 75.4-75.7° C.
  Empty Collector Weight: 227.2 g
  Run Time: 15.25 min.
  Post Run Collector Weight: 268.8 g
  Powder Collected: 41.6 g
  Powder Spray Dried: 45.8 g
  Yield: 91%

Spray Drying Run Number 88-3
  Solution 1: Raffinose/Leucine
    Solids Content (weight percent): 5.5% (~91% Raffinose, ~9% Leucine)
    Number of Nozzles: 2
    Total Flow Rate: 30 ml/min (15 ml/min per nozzle)
  Solution 2: Water
    Solids Content (weight percent): n/a
    Number of Nozzles: 3
    Total Flow Rate: 30 ml/min (10 ml/min per nozzle)
  Dryer Initial Condition: Clean
  Atomizer Pressure: 40 psig
  Total Dryer Flow Rate: 110 SCFM
  Dryer Inlet Temperature: 195° C.
  Dryer Outlet Temperature: 75.2-75.6° C.
  Empty Collector Weight: 226.3 g
  Run Time: 30.00 min.

Post Run Collector Weight: 259.5 g
Powder Collected: 33.2 g
Powder Spray Dried: 49.5 g
Yield: 67%

Spray Drying Run Number 89-4
Solution 1: Raffinose
  Solids Content (weight percent): 10%
  Number of Nozzles: 2
  Total Flow Rate: 30 ml/min (15 ml/min per nozzle)
Solution 2: Leucine
  Solids Content (weight percent): 1%
  Number of Nozzles: 3
  Total Flow Rate: 30 ml/min (10 ml/min per nozzle)
Dryer Initial Condition: Clean
Atomizer Pressure: 40 psig
Total Dryer Flow Rate: 110 SCFM
Dryer Inlet Temperature: 195° C.
Dryer Outlet Temperature: 74.7-75.4° C.
Empty Collector Weight: 226.1 g
Run Time: 25.5 min.
Post Run Collector Weight: 298.2 g
Powder Collected: 72.1 g
Powder Spray Dried: 84.2 g
Yield: 86%

Powder Sampling

In a glovebox at less than 3% RH at ambient temperature, the collector was opened and the spray-dried powder was poured in a continuous "S" shape into a 4" square-bottomed weighing dish. For the raffinose/leucine blend, nine evenly spaced imaginary points in the plane of the powder sample were selected as sampling locations. Using a small spatula, approximately 5 mg of powder from each location were dispensed into a pre-weighed empty 15 ml centrifuge tube. As a measure of the reproducibility of the steps in the assay, five samples were collected from the center point of the sample array. A similar procedure was performed for the raffinose/leucine powder spray-dried from a single solution, except samples were collected only from each of the four corners of the weighing dish.

To eliminate differences in water contents among samples of a given powder, all weighing was performed at controlled relative humidity (RH) and temperature (40% RH/70° F.). To ensure a consistent water content, all samples were exposed to 40% RH/70° F. for more than 24 hours. Following exposure, each sample tube was reweighed, and the mass of RH-equilibrated powder was determined by difference.

Moisture Content Determination

For experiments to determine the moisture content of each lot of powder, approximately 10 mg of powder were sampled from each of the four corners of the weighing dish and then combined into a single sample. The composite sample was then stored under the same conditions (time, temperature, RH) as the samples for leucine content determination. Following exposure, samples were prepared in triplicate for moisture content determination by thermogravimetric analysis (TGA). A TA Instruments Hi-Res TGA 2950 was used to measure the mass loss upon heating of each powder sample. About 8 to 12 mg of each powder was packed into a small aluminum pan, which was then hermetically sealed. Immediately prior to each TGA experiment, the lid of the pan was pierced. Using this technique, water content is determined from the mass loss upon drying at elevated temperature. A previously developed method was used to ensure that the temperatures used did not result in volatilization of either raffinose or leucine.

Leucine Content Determination

To quantitate leucine content in each of the powders, a Dionex liquid chromatographic system was used. Leucine was eluted isocratically through a CarboPac PA10 analytical 4 mm column, attached to a guard 4 mm column, using a mobile phase consisting of a 50:50 mixture of Mobile Phase A (200 mM sodium hydroxide) and Mobile Phase B ("Milli-Q" water). At a flow rate of 1 mL/min, leucine was eluted within a 13-minute runtime. By preparing leucine solutions of known concentration, a calibration curve of integrated peak area vs. concentration was generated for concentrations between 0.05 mM and 0.6 mM (millimoles/liter).

To measure the leucine content of each powder sample, it was necessary to rehydrate the sample with enough water so that the leucine concentration was within the range of the calibration curve. A calibrated pipette was used to rehydrate each powder with 14.00 ml $H_2O$. The samples were sonicated to ensure complete dissolution of powder, and vials were then prepared for automated injection into the Dionex system.

Data Analysis

The previously measured (on the same day) calibration curve was used to determine the leucine concentration of each rehydrated sample based on the average integrated peak area from two injections. The mass of leucine in the original powder sample was then calculated by:

$$\text{mg leucine} = M_{leucine}(\text{mol}/\text{l}) \times V_{rehydrated} \times \frac{131.18 \text{ g leucine}}{\text{mol leucine}} \times 1000 \frac{\text{mg}}{\text{g}} \quad [1]$$

where $M_{leucine}$ is the leucine concentration based on the calibration curve 131.18 is the molecular weight of L-leucine, and 1000 is a conversion factor from mg to g. In principle, $V_{rehydrated}$ should be the total volume of the rehydrated powder. However, since the mass of powder relative to the mass of water is small enough, the small volume of the powder can be neglected and $V_{rehydrated}$ is taken to be the volume of water (14.00 ml) used to rehydrate the powder.

The mass of water in each powder sample was calculated from the average water content measured using TGA, wt % $H_2O$, given by:

$$\text{mg } H_2O = \frac{\text{wt \% } H_2O}{100} \times \text{mg powder} \quad [2]$$

where mg powder is the mass of the original powder sample.

The raffinose content in the original powder sample was then calculated by subtracting from the total mass of powder the masses of leucine and water. In this work, the leucine/raffinose ratio is used as the concentration variable.

$$\text{mg raffinose} = \text{mg powder} - \text{mg leucine} - \text{mg } H_2O \quad [3]$$

Figure 10:
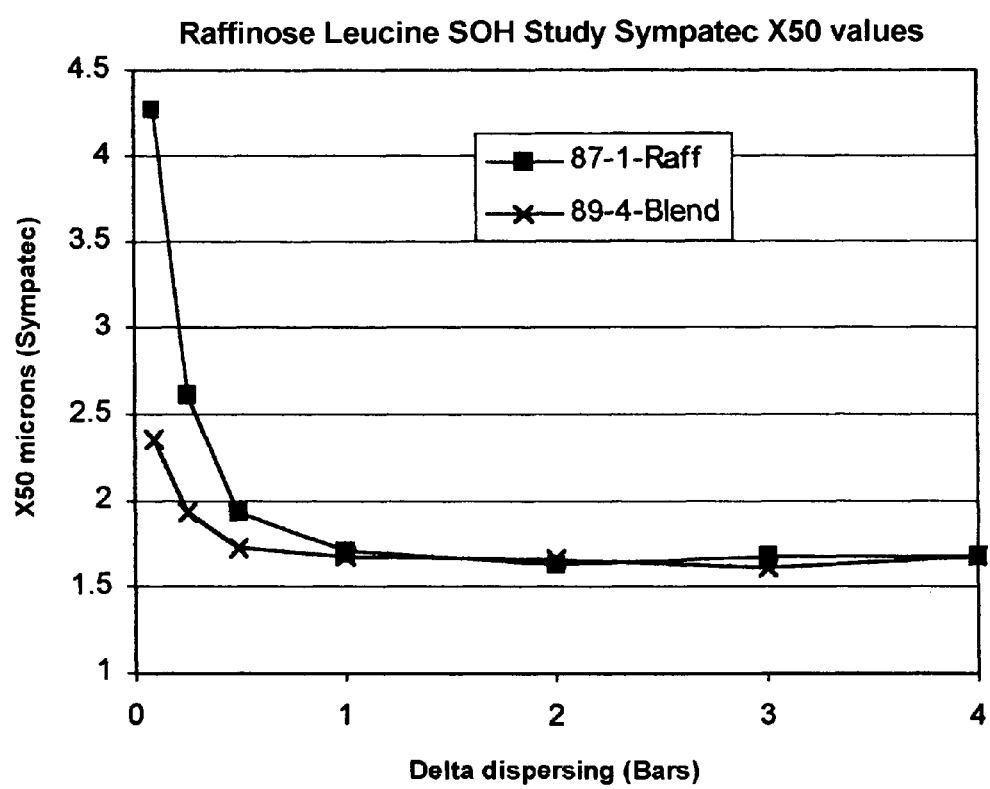
FIG. 10 depicts a plot of median size vs. dispersion pressure for various formulations prepared according to the invention.

The X50 (median) size of the neat Raffinose and the blended raffinose/Leucine (10:1 mass ratio) powders, as determined by a Sympatec laser diffraction instrument after being dispersed through Sympatec's Rodos dry powder dispersing system at different dispersing pressures are shown in Table 5 and FIG. 10. At low dispersing pressures the powder is not fully dispersed to 'primary' particles, so the Sympatec measures the size of the agglomerates that pass through the Rodos disperser. At sufficiently high dispersing pressures the agglomerates are dispersed into their constituent primary particles. At high Rodos dispersing pressures the two powders exhibited nearly the same X50 size of approximately 1.66

(+−2%) microns. These data show that the neat Raffinose powder has agglomerates of median size approximately 2.5 times the primary particle size when weakly dispersed with only 0.1 bar of dispersing pressure in the Rodos disperser. The blended powder has a median agglomerate size that is only 1.4 times the primary particle size at the same dispersing pressure. Also, the neat Raffinose powder requires dispersing pressures exceeding 1 bar to fully disperse to primary particles, while the blended powder is similarly dispersed with half as much dispersing pressure through the Rodos disperser. This provides another indication of the improved dispersibility of the powder blends produced according to this invention.

TABLE 5

| Dispersing Pressure | Lot 87-1-neat Raffinose | Lot 89-4-Blend Raffinose/Leucine |
|---|---|---|
| 0.1 | 4.28 | 2.36 |
| 0.25 | 2.61 | 1.94 |
| 0.5 | 1.94 | 1.73 |
| 1 | 1.71 | 1.67 |
| 2 | 1.63 | 1.66 |
| 3 | 1.68 | 1.61 |
| 4 | 1.67 | 1.67 |

Results

Figure 8:
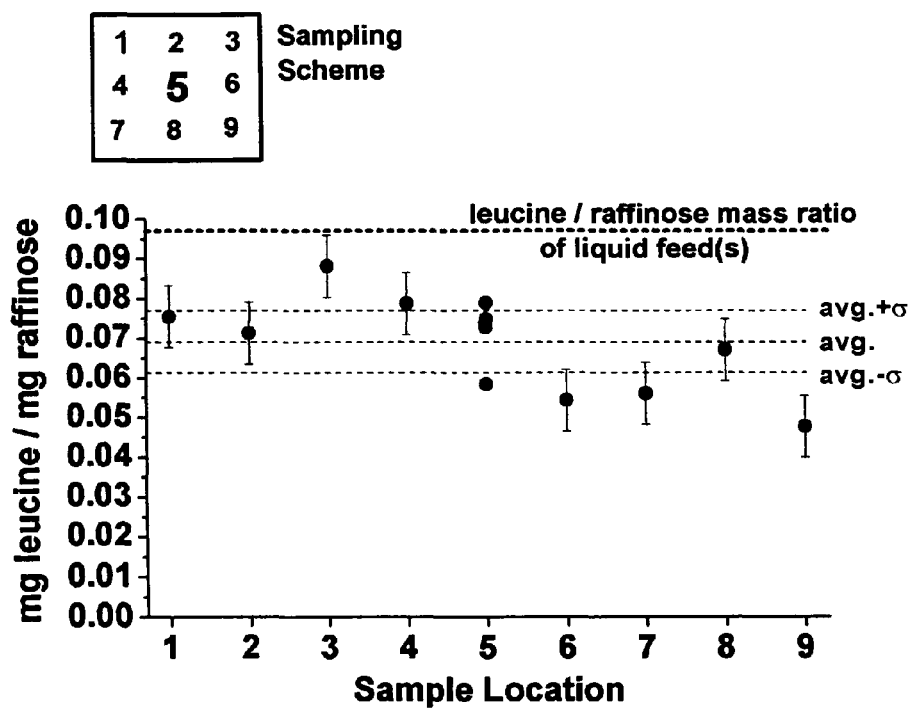
FIG. 8 depicts blend uniformity plot according to the invention.
Figure 9:
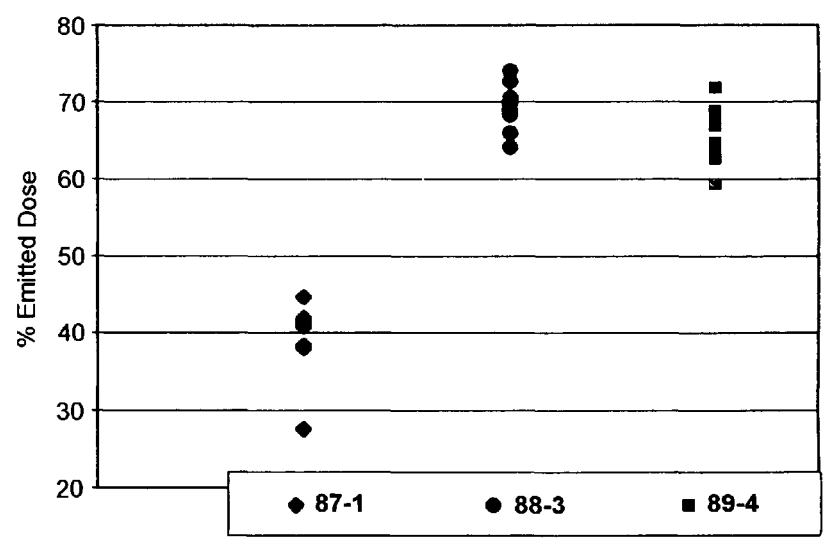
FIG. 9 depicts emitted dose data of various formulations prepared according to the invention.

The blend uniformity of the raffinose/leucine blend is depicted in FIG. 8. FIG. 9 depicts the emitted dose data for the powders prepared in runs 87-1, 88-2, and 89-4.

Having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A method for making a powder pharmaceutical for pulmonary administration, the method comprising:
   providing a feedstock containing an active agent in a liquid vehicle, wherein the active agent comprises one or more of an antibiotic, an anti-inflammatory agent, and a bronchodilator;
   providing a multi-nozzle atomizer comprising a housing supporting a central gas nozzle and a plurality of atomization nozzles around the central gas nozzle, wherein each atomization nozzle comprises a liquid nozzle and a gas nozzle that is configured as a cap surrounding the liquid nozzle, and wherein the central gas nozzle is not associated with a liquid nozzle;
   atomizing the feedstock from the multi-nozzle atomizer to produce a droplet spray, wherein the feedstock is fed through the housing to the liquid nozzles in each of the atomization nozzles; and
   flowing the droplet spray in a heated gas stream to evaporate the liquid vehicle of the feedstock and produce a powder of dry particulates comprising the active agent, wherein the dry particulates have an average particle size of less than 5 microns.

2. The method of claim 1, wherein the total dissolved or suspended solids content in the feedstock is within a range from 0.5% to 10% by weight.

3. The method of claim 1, wherein a throughput of the feedstock is at least 500 mL/min.

4. The method of claim 1, wherein the powder comprises an ultrafine dry powder for pulmonary administration.

5. The method of claim 1, wherein the dry particulates have a rugosity of greater than 2.0.

6. The method of claim 1, wherein the dry particulates have a substantially smooth surface.

7. The method of claim 1, wherein the feedstock further comprises at least one excipient.

8. The method of claim 1, wherein the multi-nozzle atomizer comprises at least three atomization nozzles.

9. The method of claim 1, wherein the multi-nozzle atomizer comprises at least four atomization nozzles.

10. The method of claim 1, wherein the multi-nozzle atomizer comprises at least five atomization nozzles.

11. The method of claim 1, wherein the multi-nozzle atomizer comprises an atomizer centerline, and wherein each of the plurality of atomization nozzles is disposed at an angle away from the atomizer centerline.

12. The method of claim 11, wherein the angle away from the atomizer centerline ranges from 10° to 40°.

13. The method of claim 11, wherein the central gas nozzle has an axis substantially along the atomizer centerline.

14. The method of claim 1, wherein the feedstock is from a single source.

15. A method for making a powder pharmaceutical for pulmonary administration, the method, comprising:
   providing a feedstock containing an active agent in a liquid vehicle, wherein the active agent comprises an antibiotic, wherein the antibiotic comprises one or more of ciprofloxacin, tobramycin, clarithromycin, gentamicin, and azithromycin;
   providing a multi-nozzle atomizer comprising a plurality of atomization nozzles, wherein each atomization nozzle comprises a liquid nozzle and a gas nozzle;
   atomizing the feedstock from the multi-nozzle atomizer to produce a droplet spray, wherein the feedstock is from a single source and is fed to the liquid nozzles in each of the atomization nozzles; and
   flowing the droplet spray in a heated gas stream to evaporate the liquid vehicle of the feedstock and produce a powder of dry particulates comprising the active agent, wherein the dry particulates have an average particle size of less than 5 microns.

16. The method of claim 15 wherein the multi-nozzle atomizer comprises a housing supporting a central gas nozzle and a plurality of atomization nozzles around the central gas nozzle.

17. The method of claim 15, wherein the total dissolved or suspended solids content in the feedstock is within a range from 0.5% to 10% by weight.

18. The method of claim 15, wherein a throughput of the feedstock is at least 500 mL/min.

19. The method of claim 15, wherein the dry particulates have a rugosity of greater than 2.0.

20. A method for making a powder pharmaceutical for pulmonary administration, the method comprising:
   providing a feedstock containing an active agent in a liquid vehicle;
   providing a multi-nozzle atomizer comprising a housing supporting a central gas nozzle and a plurality of atomization nozzles around the central gas nozzle, wherein each atomization nozzle comprises a liquid nozzle and a gas nozzle that is configured as a cap surrounding the liquid nozzle, and wherein the central gas nozzle is not associated with a liquid nozzle, wherein each of the plurality of atomization nozzles is disposed at an angle away from the atomizer centerline that ranges from 10° to 40°;

atomizing the feedstock from the multi-nozzle atomizer to produce a droplet spray, wherein the feedstock is fed through the housing to the liquid nozzles in each of the atomization nozzles; and flowing the droplet spray in a heated gas stream to evaporate the liquid vehicle of the feedstock and produce a powder of dry particulates comprising the active agent, wherein the dry particulates have an average particle size of less than 5 microns.

21. The method of claim 20, wherein a throughput of the feedstock is at least 500 mL/min.

22. The method of claim 20, wherein the feedstock is from a single source.

23. The method of claim 20, wherein the dry particulates have a rugosity of greater than 2.0.

24. The method of claim 20, wherein the multi-nozzle atomizer comprises at least three atomization nozzles.

25. The method of claim 20, wherein the multi-nozzle atomizer comprises at least four atomization nozzles.

26. The method of claim 20, wherein the multi-nozzle atomizer comprises at least five atomization nozzles.

* * * * *